(12) United States Patent
Kawashima et al.

(10) Patent No.: US 7,540,614 B2
(45) Date of Patent: Jun. 2, 2009

(54) OPHTHALMOLOGIC APPARATUS

(75) Inventors: Hiroyuki Kawashima, Tokyo (JP); Gaku Takeuchi, Tokyo (JP); Takao Tanabe, Tokyo (JP); Noriyasu Kiryu, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 0 days.

(21) Appl. No.: 12/005,275

(22) Filed: Dec. 27, 2007

(65) Prior Publication Data

US 2008/0158508 A1 Jul. 3, 2008

(30) Foreign Application Priority Data

Dec. 28, 2006 (JP) .............................. 2006-353713

(51) Int. Cl.
*A61B 3/14* (2006.01)
*A61B 3/10* (2006.01)

(52) U.S. Cl. ..................... 351/206; 351/205; 351/208

(58) Field of Classification Search .......... 351/205–246
See application file for complete search history.

(56) References Cited

U.S. PATENT DOCUMENTS

2002/0159029 A1* 10/2002 Ross et al. ................. 351/212
2003/0053028 A1* 3/2003 Wirth ........................ 351/221
2005/0083430 A1 4/2005 Hirasawa et al.
2005/0207037 A1* 9/2005 Minegishi ................... 359/846

FOREIGN PATENT DOCUMENTS

JP 2005-221579 8/2005

OTHER PUBLICATIONS

Extended European Search Report dated May 30, 2008 issued in EP Application No. 07025133.5-2319.

* cited by examiner

*Primary Examiner*—Mohammed Hasan
(74) *Attorney, Agent, or Firm*—Dickstein Shapiro LLP (57) ABSTRACT

An ophthalmologic apparatus includes an imaging system that illuminates a retina of an eye, and images the retina of the eye based on reflective luminous flux from the retina, an aberration measurement part that measures optical aberration of the eye, an aberration compensation device disposed in the imaging system to compensate the optical aberration of the eye based on a signal from the aberration measurement part, a first focusing device disposed in an optical path of the imaging system to perform focusing of the image of the retina of the eye according to a refractive property of the eye, and a second focusing device disposed in the optical path of the imaging system to compensate infinitesimal spherical aberration generated by the aberration compensation device after adjustment by the first focusing device.

6 Claims, 8 Drawing Sheets

ARRANGEMENT
EXAMPLE OF ELECTRODE

FIG.6

SIDE OF ELECTRODE

FIG. 7

OPHTHALMOLOGIC APPARATUS

PRIORITY CLAIM

This application claims priority from Japanese Patent Application No. 2006-353713, filed with the Japanese Patent Office on Dec. 28, 2006, the contents of which are incorporated herein by reference in their entirety.

BACKGROUND OF THE INVENTION

1. Field of the Invention

The present invention relates to an ophthalmologic apparatus that can perform observation, photographing, and capturing of image data of a clear retinal image with high magnification by adding an aberration compensation function that corrects wavefront aberration.

2. Description of Related Art

Conventionally, a retinal camera is known that performs observation and photographing of a retina by imaging the retina based on the reflected luminous flux from the illuminated retina. However, because the reflected luminous flux of the retina passes through an ocular optical system formed by a cornea, a crystalline lens, a vitreous body and so on, due to the effects of aberration of the ocular optical system, the retinal camera of this kind has a problem of not being able to obtain an image of a retina with high resolution as well as a clear image of a retina having high magnification. Incidentally, the ocular optical system is far from an ideal optical element, possesses optical refractive properties which generate various aberrations such as myopia and astigmatism, and the wavefront due to the reflected luminous flux from the retina has distortions.

On the other hand, an apparatus is proposed to obtain a clear image of a retina, having high magnification provided with an aberration measurement part which measures optical aberration of an eye and an aberration compensation part such as a deformable mirror for compensating the distortions of the wavefront of the reflected luminous flux caused by the optical aberration of the eye based on the signals from the aberration measurement part (refer to JP 2005-221579A).

Howeyer, since it is difficult to broaden the compensation range of a deformable mirror on the apparatus that uses the deformable mirror to compensate the aberration, the spherical diopter and the astigmatism diopter of the eye are compensated by adjusting an astigmatism compensation lens and a focusing lens disposed in a photographing system before photographing. The deformable mirror thereby compensates the remaining part of the compensation and higher-order aberration component. Hereby, the stroke of the focusing lens is quite large because it corresponds to hyperopia and myopia.

By the way, this deformable mirror generates a high-order aberration component by deforming a membrane as a reflective mirror into a desired shape. Since the membrane is deformed with only the electrostatic force by applying desired voltages to the electrodes disposed to face the membrane, it is inevitable that an infinitesimal spherical diopter is newly generated due to the deformation.

In order to solve this problem, it is thought that further compensation and adjustment by the focusing lens are required. However, since it is problematic that the accuracy and responsiveness will be low by the adjustment of the focusing lens, as a matter of practice, the compensation and the adjustment by the focusing lens can not be made. Consequently, the conventional technologies cannot perform high speed aberration compensation in correspondence to the infinitesimal spherical diopter newly generated by the deformable mirror, and it is problematic that the aberration by the infinitesimal spherical diopter will remain.

SUMMARY OF THE INVENTION

The present invention is made with regard to the above problematic points, and it is an object of the present invention to provide an ophthalmologic apparatus that can capture an extremely clear retina image eyen with high magnification with high accuracy and high speed by compensating an infinitesimal spherical aberration newly generated accompanying aberration compensation.

To attain the above object, the present invention relates to an ophthalmologic apparatus including an imaging system that illuminates a retina of an eye, and images the retina of the eye based on reflective luminous flux from the retina, an aberration measurement part that measures optical aberration of the eye, an aberration compensation device disposed in the imaging system to compensate the optical aberration of the eye based on a signal from the aberration measurement part, a first focusing device disposed in an optical path of the imaging system to perform focusing of the image of the retina of the eye according to a refractive property of the eye, and a second focusing device disposed in the optical path of the imaging system to compensate an infinitesimal spherical aberration generated by the aberration compensation device after adjustment by the first focusing device.

BRIEF DESCRIPTION OF THE DRAWINGS

These and other features, aspects, and advantages of the present invention will become better understood with regard to the following description, appended claims, and accompanying drawings.

DETAILED DESCRIPTION OF THE INVENTION

An embodiment for realizing an ophthalmologic apparatus according to the present invention will be described hereinbelow with reference to the accompanying drawings.

Embodiment 1

First, the constitution will be described.

[Exterior Constitution]

Figure 1:
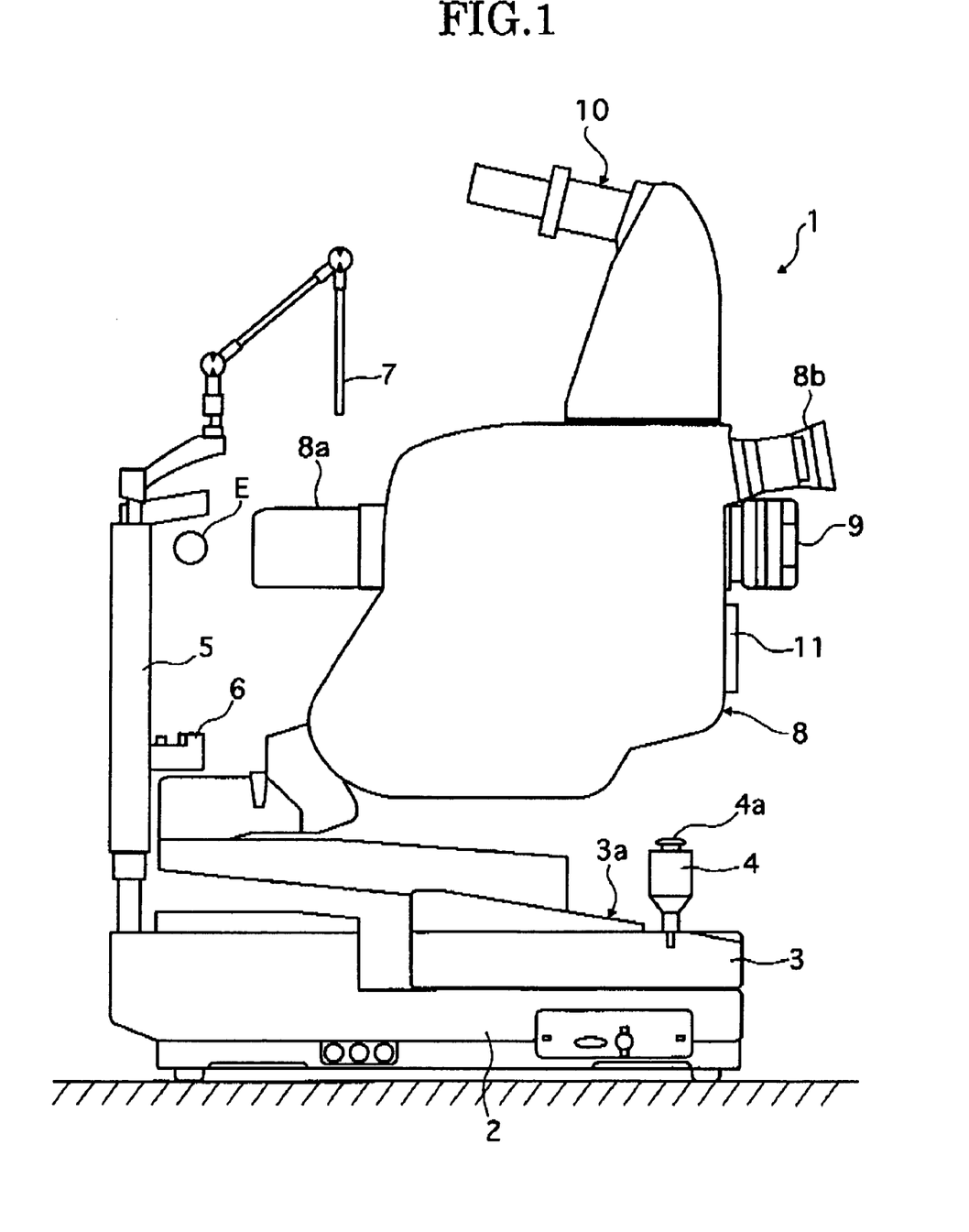
FIG. 1 is an exterior lateral view that illustrates an example of an ophthalmologic apparatus 1 applied with an AO system of embodiment 1.

FIG. 1 is an exterior lateral view illustrating one example of an ophthalmologic apparatus 1 applied with an AO system of embodiment 1. The exterior constitution is explained based on FIG. 1 hereinbelow. In addition, "the AO system (adaptive optics system)" is also termed as a compensation optics system. This is a system that has the function of negating wavefront aberration by a deformable minor.

The ophthalmologic apparatus 1 of the embodiment 1, as illustrated in FIG. 1, includes a base 2, and a trestle 3 slidably mounted on the base 2 in a back-and-forth and right-and-left direction (horizontal direction).

A control leyer 4 is disposed on the trestle 3. An examiner can operate the control leyer 4 to freely move the trestle 3 on the base 2. In addition, a photographing button 4a is disposed on the head portion of the control leyer 4, so that a retina image can be photographed by the operation of a button.

A column 5 is uprightly disposed on the base 2. A chin rest 6 onto which a chin part of an examinee is placed, and an exterior fixation lamp 7 that is the light source for fixing an eye E are provided in the column 5.

A main body part 8 is disposed on the trestle 3 and stores a wide variety of optical systems of the ophthalmologic apparatus 1. The rain body part 8 is provided with an objective lens part 8a disposed to face the eye E and an ocular lens part 8b to perform the observation or the like of the eye E by the examiner.

Also, a first imaging device 9 such as a CCD camera to photograph a still image of the retina of the eye E, a second imaging device 10 such as a television camera to photograph the in a image of the eye E and a third imaging device in the form of a microscope unit and so on (not shown) are connected to the main body part 8. In addition, these imaging devices have digital imaging methods. Thereby, these imaging devices can send image data to a computer (not shown) disposed outside the ophthalmologic apparatus 1, and conduct monitor display, the recording of the image data, and the photographing of the retina.

A color liquid crystal monitor 11 is disposed on the examiner's side of the main body part 8. This color liquid crystal monitor 11 performs monitor display of the retina image of the eye E based on the picture signals captured by the second imaging device 10.

A control panel 3a is disposed on the upper face part of the trestle 3. The control panel 3a includes a display part and buttons to perform various settings, the confirmation of photographing conditions, and the like.

[Optical System Constitution]

Figure 2A:
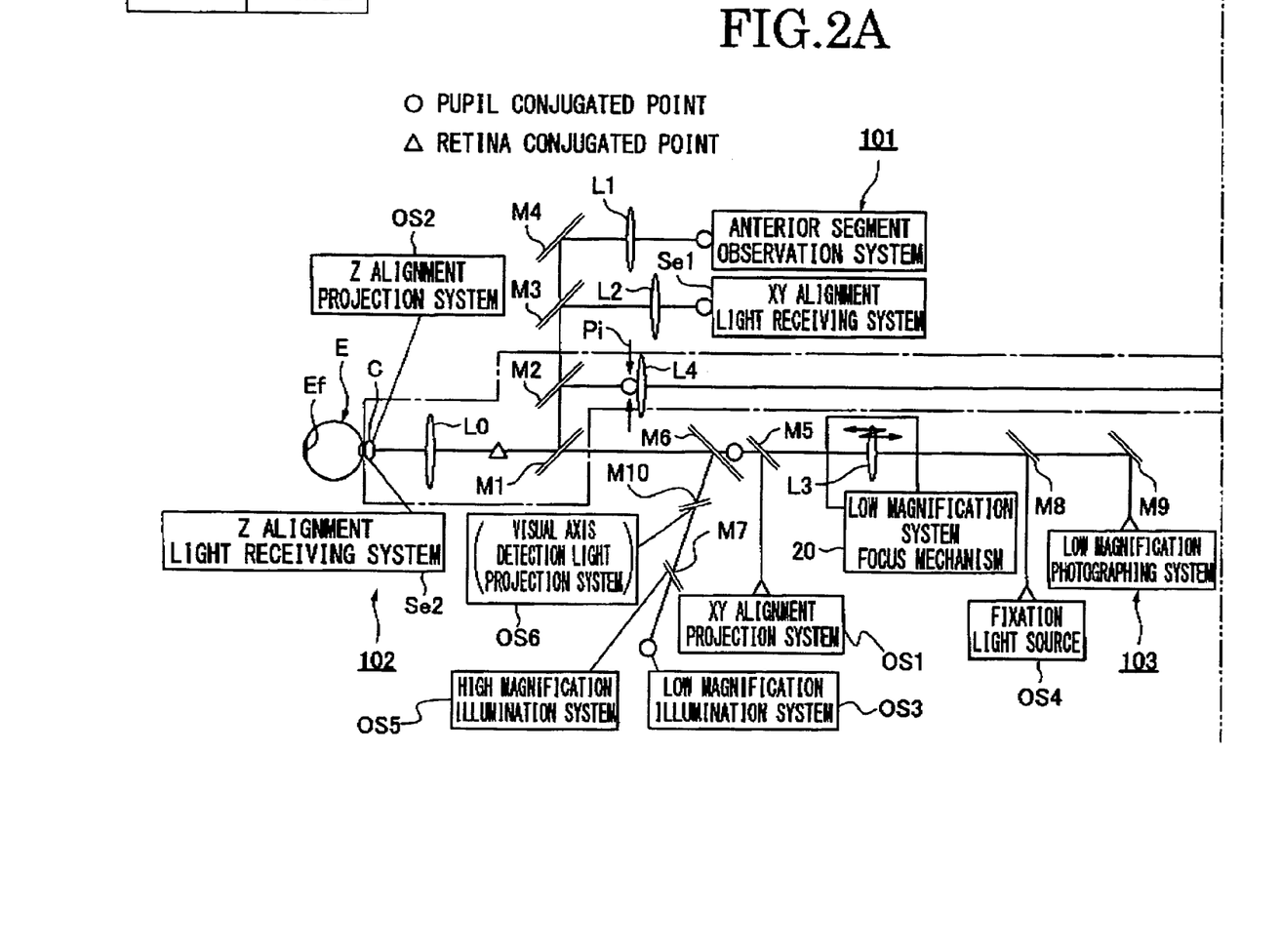
FIG. 2 is a schematic view that illustrates an example of a configuration of an optical system by the AO system stored in a main body part 8 of the ophthalmologic apparatus 1 of embodiment 1.
Figure 2B:
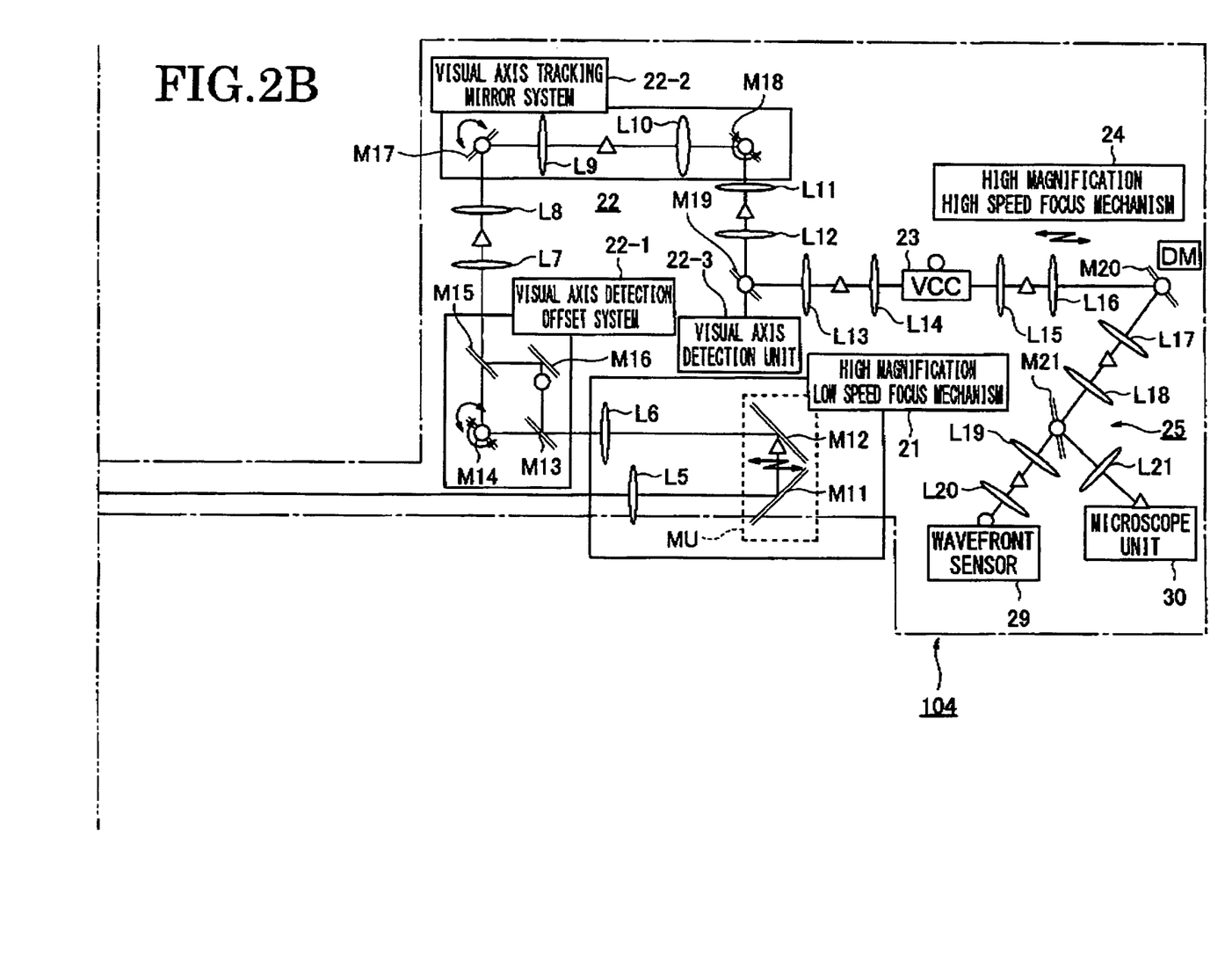

FIG. 2 is a schematic view illustrating an example of an optical system constitution by the AO system stored in the main body part 8 of the ophthalmologic apparatus 1 of the embodiment 1. In addition, in FIG. 2, O indicates a pupil conjugated point that forms an image of a pupil of the eye E based on the reflected luminous flux, and Δ indicates a retina conjugated point that forms an image of a retina Ef of the eye E based on the reflected luminous flux.

The optical system of the ophthalmologic apparatus 1 includes an anterior segment observation system 101 that observes an anterior segment of the illuminated eye E, an alignment detection system 102 used to perform precise alignment relative to the eye E, a low-magnification retina photographing system 103 that observes and photographs the retina Ef of the illuminated eye E, and a high-magnification retina photographing system 104 that observes and photographs the retina Ef of the illuminated eye E.

Hereinbelow, the constitution of the optical system is described based on FIG. 2 by separating the constitution of the optical system into the constitution of a retinal camera corresponding optical system and the constitution of the high magnification retina photographing system.

[The Constitution of an Optical System Corresponding to the Retinal Camera]

The anterior segment observation system 101 includes an anterior segment illumination light source (not shown) that illuminates the anterior segment of the eye E, for an imaging system that observes the anterior segment of the eye E based on the reflected luminous flux from the anterior segment an objective lens L0, a half mirror M1, dichroic mirrors M2, M3, a mirror M4, and an ocular lens L1. The examiner (observer or photographer) observes on a monitor screen the anterior segment image imaged on the anterior segment observation system 101 and moves by manual operation the main body part 8 of the ophthalmologic apparatus 1, performs the approximate alignment of the main body part 8 relative to the eye E.

An XY alignment detection system of the alignment detection system 102 includes between an XY alignment projection system OS1 and the cornea C of the eye E, an alignment mirror M5, a perforated mirror M6, the half mirror M1, and the objective lens L0. Also, the XY alignment detection system of the alignment detection system 102 includes between the cornea C of the eye E and an XY alignment light receiving system Se1 the objective lens L0, the half mirror M1, the dichroic mirrors M2, M3 and a lens L2. A Z alignment detection system of the alignment detection system 102 includes a Z alignment projection system OS2 on one side and a Z alignment light receiving system Se2 on the other side across from the cornea C of the eye E. The alignment detection system 102 is used to automatically perform precise alignment of the main body part 8 relative to the eye E after the approximate alignment of the apparatus main body relative to the eye E is completed by the anterior segment observation system 101. In addition, the principle of the alignment of this alignment detection system 102 is well known, so the detailed description is abbreviated.

The low-magnification retina photographing system 103 includes an illumination system, an imaging system and a fixation target system. The illumination system that illuminates the retina Ef of the eye E by light from a low-magnification illumination system OS3 (for example, a halogen lamp) includes a dichroic mirror M7, a dichroic mirror M10, the perforated mirror M6, the half mirror M1, and the objective lens L0

The imaging system that images the retina image of the eye E based on the reflected luminous flux from the retina Ef includes the objective lens L0, the half mirror M1, the perforated mirror M6, the alignment mirror M5, a low-magnification system focus mechanism 20, a dichroic mirror M8, and a mirror M9. In addition, the low magnification system focus mechanism 20 is used to compensate the anomalies of refraction of an eyeball by moving forward and backward a diopter compensation lens L3 along the optical axis.

The fixation target system that forms a fixation target light source image on the retina Ef includes a fixation light source OS4 that emits fixation target light towards the dichroic mirror M8. The visual axis direction of the eye E is determined by the projection of fixation target.

The anterior segment observation system 101, the alignment detection system 102 and the low-magnification retina photographing system 103 are optical systems corresponding to conventional retinal cameras. Along with being used to perform the observation of the retina Ef in a broad visual field, they are also used to determine the photographing position when photographing with high magnification.

[The Constitution of High Magnification Retina Photographing System]

The high-magnification retina photographing system 104 includes an illumination system that illuminates the retina Ef of the eye E, and an imaging system that images the retina image of the eye E based on the reflected luminous flux from the retina Ef. The optical path of the imaging system includes a high-magnification low-speed focus mechanism 21 (the first focusing device), a visual axis tracking control system 22, a cylinder component adjustment mechanism 23 (the first focusing device), a high-magnification high-speed focus mechanism 24 (the second focusing device), and a wavefront aberration compensation system 25 (aberration compensation device). Each constitution is described hereinbelow.

Illumination System

The illumination system that illuminates the retina Ef of the eye E includes a high magnification illumination system OS5 (for example, a xenon lamp), the dichroic mirror M7, the dichroic mirror M10, the perforated mirror M6, the half mirror M1 and the objective lens L0.

The reflected luminous flux from the retina Ef is led to the high-magnification low-speed focusing mechanism 21 passing through the objective lens L0, the half mirror M1, the dichroic mirror M2, a throttle plate pi and a lens L4.

High-magnification Low-speed Focusing Mechanism 21

The high-magnification low-speed focusing mechanism 21 includes a lens L5 disposed on the input side of the reflected luminous flux from the retina Ef, a mirror unit MU (reflective member) provided with two orthogonal mirrors M11, M12 (reflective part) disposed within the optical path of the imaging system, and a lens L6 disposed on the output side of the reflected luminous flux from the mirror unit MU.

By way of a first focus adjustment motor actuator 26 (the first motor device, refer to FIG. 3), the mirror unit MU adjusts the optical path length by moving along the optical axis direction.

The high-magnification low-speed focusing mechanism 21 is a focusing device that performs the focusing of the retina image of the eye E according to the refractive property of the eye E. The high-magnification low-speed focusing mechanism 21 compensates the spherical diopter power component (myopia, hyperopia and so on) of the wavefront aberration generated because of the refractive property of the eye E.

The Visual Axis Tracking Control System 22

The visual axis tracking control system 22 detects a visual axis direction of an eye to remove the movement of a retina image due to the deflection of the visual axis direction. Based on the detection results, the visual axis tracking control system 22 performs trucking relative to the retina. That is to say, an eyeball always continues infinitesimal motion called involuntary eye movement. By this involuntary eye movement the visual axis direction always moves, the retina image to be imaged oscillates, and blurring of the retina image is generated, so that particularly when observing the retina image with high resolution at the visual cell leyel, it is necessary to remove the influence of such involuntary eye movement.

An illumination system to floodlight visual axis detection light of the visual axis tracking control system 22 includes a visual axis detection light projection system OS6, the dichroic mirror M10, the perforated mirror M6, the half mirror M1, and the objective lens L0.

A visual axis detection offset system 22-1 of the visual axis tracking control system 22 includes a dichroic mirror M13 disposed on the optical axis to input the reflected luminous flux and the visual axis detection light from the lens L6, a visual axis detection optical axis offset mirror M14, a dichroic mirror M15, and a mirror M16.

When the visual axis detection optical axis offset mirror M14 is inclined two-dimensionally (X direction, Y direction), the retina position of the tracking target is selected randomly. Howeyer, the dichroic mirrors M13 and M15 bends only the visual axis detection light (near infrared ray), so that there is no influence on the reflected luminous flux from the retina Ef.

A visual axis tracking mirror system 22-2 of the visual axis tracking control system 22 includes an X direction tracking mirror M17 that deflects the optical axis which inputs the reflected luminous flux and the visual axis detection light through a lens L7 and a lens L8, a lens L9, a lens L10, and a Y direction tracking mirror M18.

A visual axis detection unit 22-3 of the visual axis tracking control system 22 performs visual axis tracking by detecting the visual axis detection light inputted via a lens L11, a lens L12 and a dichroic mirror M19 from the Y direction tracking mirror M18.

For example, when performing the tracking in the right and left direction, with respect to the amplitude center of the involuntary eye movement of the retina, in order that the average output of the visual axis detection unit 22-3 obtained by the scanning trajectory of left half side be equal to the average output of the visual axis detection unit 22-3 obtained by the scanning trajectory of the right half side, the X direction tracking mirror M17 and the Y direction tracking mirror M18 are driven and adjusted to perform the tracking adjustment relative to the retina Ef. In addition, the detection target of a detection visual field of a visual axis direction can be in an approximately circular form, and representatively can be an optic disc area or a fovea centralis retinae.

Cylinder Component Adjustment Mechanism 23

The cylinder component adjustment mechanism 23 includes an astigmatism compensation variable cross cylinder lens VCC (astigmatism compensation cylinder lens) disposed on the optical axis that inputs the reflected luminous flux from the retina Ef via a lens L13 and a lens L14 from the dichroic mirror M19.

The cylinder component adjustment mechanism 23 is a focusing device that performs the focusing of the retina image of the eye E according to the refractive property of the eye E. It compensates the astigmatism diopter component (the cylinder component) of the wavefront aberration generated because of the refractive property of the eye E.

The astigmatism compensation variable cross cylinder lens VCC includes a combination of two cylinder lenses. It compensates an axis angle and a cylindrical column diopter by turning one of the cylinder lenses around the periphery of the light axis by means of a VCC adjustment motor actuator 27 (the second motor device, refer to FIG. 3)

High-magnification High-speed Focus Mechanism 24

Of a lens L16 and a lens L15 which input the reflected luminous flux from the retina Ef from the astigmatism compensation variable cross cylinder VCC to the deformable mirror M20 disposed on the light axis, the high-magnification high-speed focus mechanism 24 includes the lens L16 as the aberration compensation lens.

The high-magnification high-speed focus mechanism 24 is a focusing device that performs the compensation of the infinitesimal spherical aberration generated by the aberration compensation system 25 after the adjustment by the high-magnification low-speed focusing mechanism 21 and cylinder component adjustment mechanism 23. The high-magnification high-speed focus mechanism 24 compensates the wavefront aberration by the infinitesimal spherical diopter newly generated by deforming the deformable mirror M20.

The aberration compensation lens L16 is controlled by a second focus adjustment piezo actuator 28 (piezo device; refer to FIG. 3) such that the infinitesimal amount of movement along the optical axis direction is controlled. The "piezo element" including the second focus adjustment piezo actuator 28 is also referred to as "piezoelectric element". It is an element having the characteristic of changing its volume when a voltage is applied. Because the amount of displacement is extremely microscopical, it is utilized when high-speed infinitesimal and precise operations are required.

Wavefront Aberration Compensation System 25

The wavefront aberration compensation system 25 includes the deformable mirror M20 disposed on the light axis that inputs the reflected luminous flux from the retina Ef via the aberration compensation lens L16, a lens L17, a lens L18, a half mirror M21, a lens L19, a lens L20 disposed on the light axis from the deformable mirror M20 to the wavefront sensor 29 (aberration compensation part), a lens L21 disposed on the light axis deflected by the half minor M21, and a microscope unit 30.

The wavefront aberration compensation system 25 is an aberration compensation device disposed in a photographing system that compensates the optical aberration of the eye E based on the detection signals from the wavefront sensor 29. The wavefront aberration compensation system 25 compensates a higher-order wavefront aberration component and the remaining component of the spherical diopter and the astigmatism diopter not being able to be corrected by the compensation of the astigmatism diopter component by the cylinder component adjustment mechanism 23 and the compensation of the spherical diopter component by the high-magnification low-speed focus mechanism 21 by deforming the deformable minor M20. In addition, the microscope unit 30 enables magnification conversion. Moreover, an external computer system is connected to the microscope unit 30, so that the observation, the photographing of the retina Ef with high magnification and the capturing of the image data are performed.

The constitution of the photographing control system of the retina Ef with high magnification by automatic focusing control is explained hereinbelow.

[High-magnification Retina Image Photographing Control System]

Figure 3:
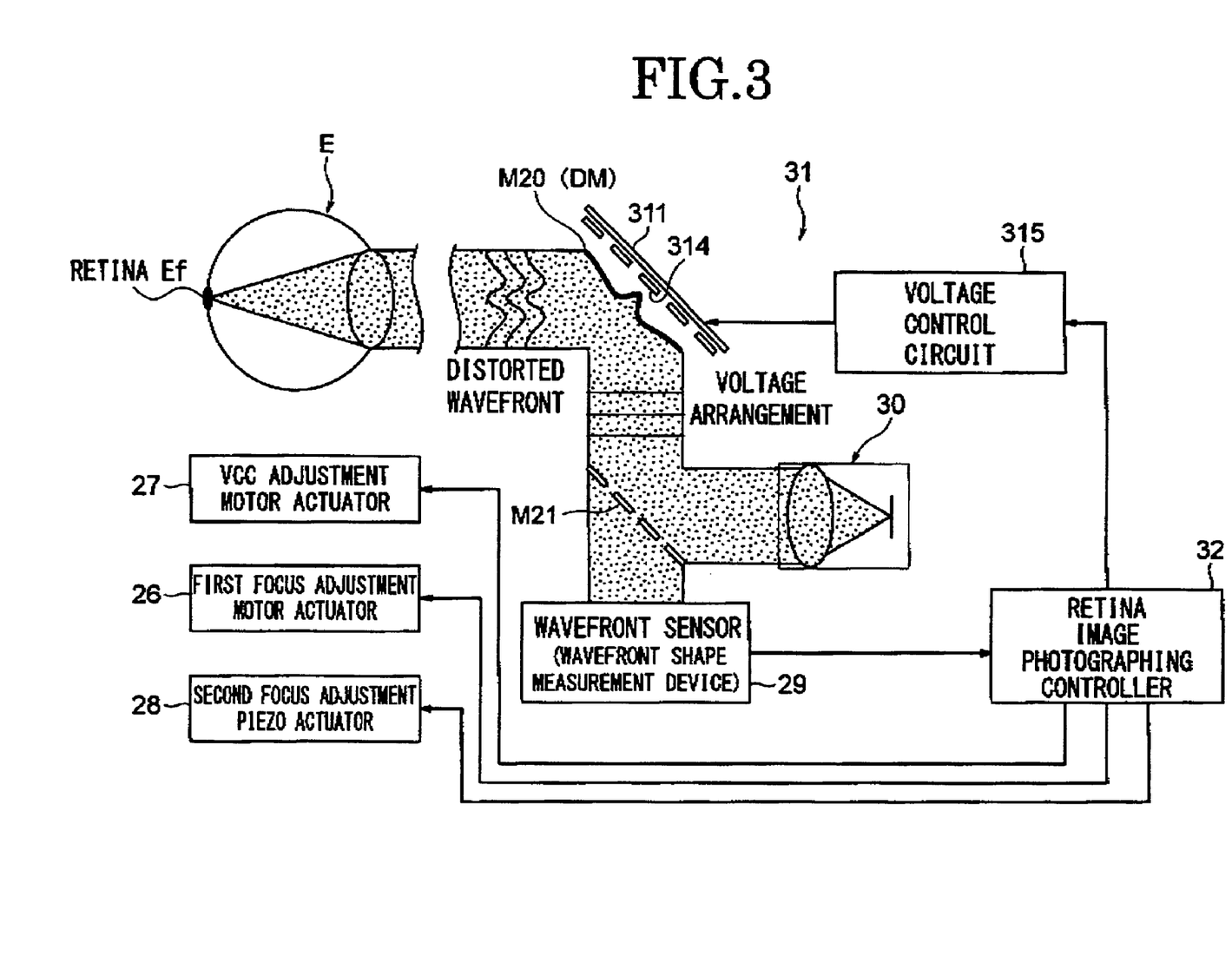
FIG. 3 is a general control system diagram that illustrates a high-magnification retina image photographing control system of embodiment 1.
Figure 4:
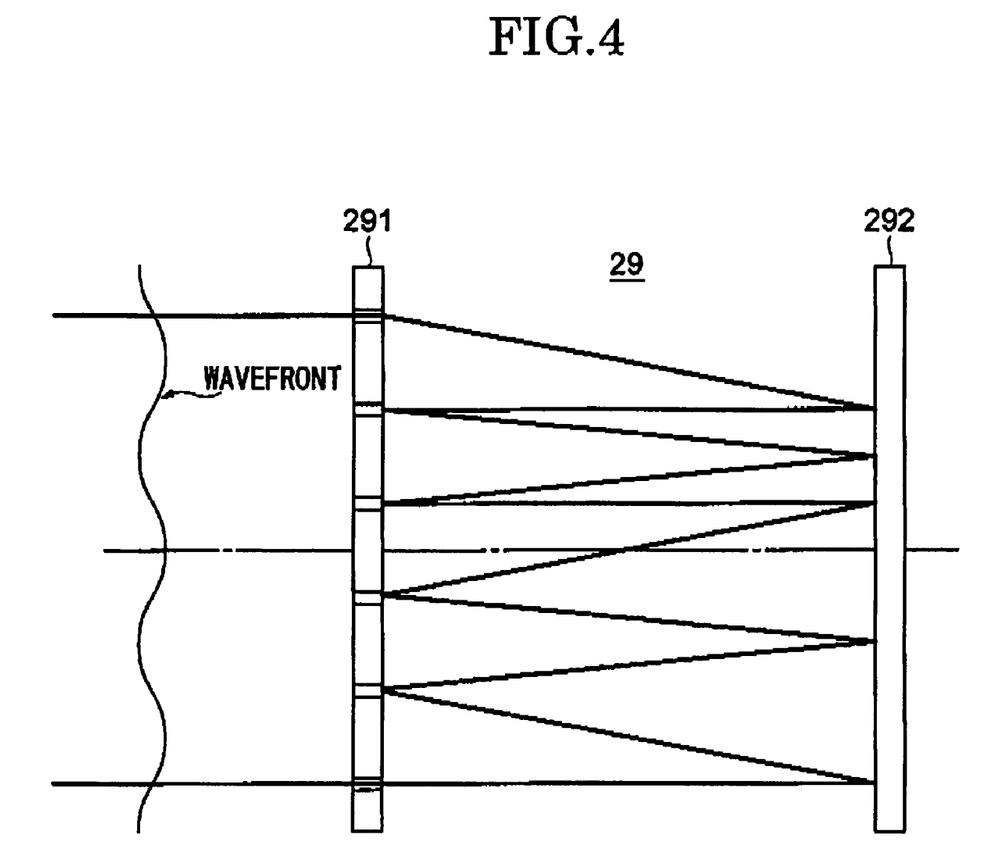
FIG. 4 is a schematic diagram that illustrates a wavefront sensor 29 of the high-magnification retina image photographing control system of embodiment 1.
Figure 5A:
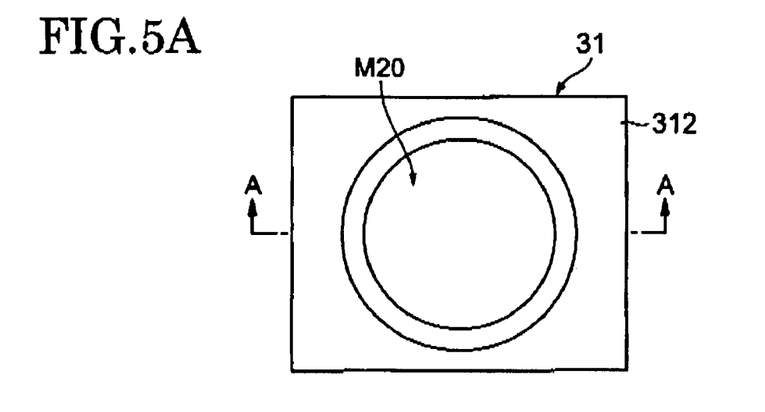
FIG. 5A is a plan view that illustrates an example of a deformable mirror device of the high-magnification retina image photographing control system of embodiment 1.
Figure 5B:
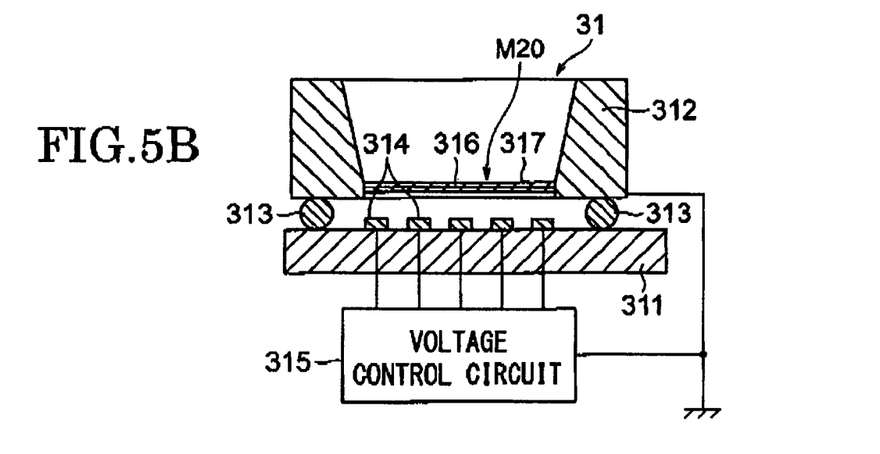
FIG. 5B is a sectional view along line A-A in FIG. 5A.
Figure 5C:
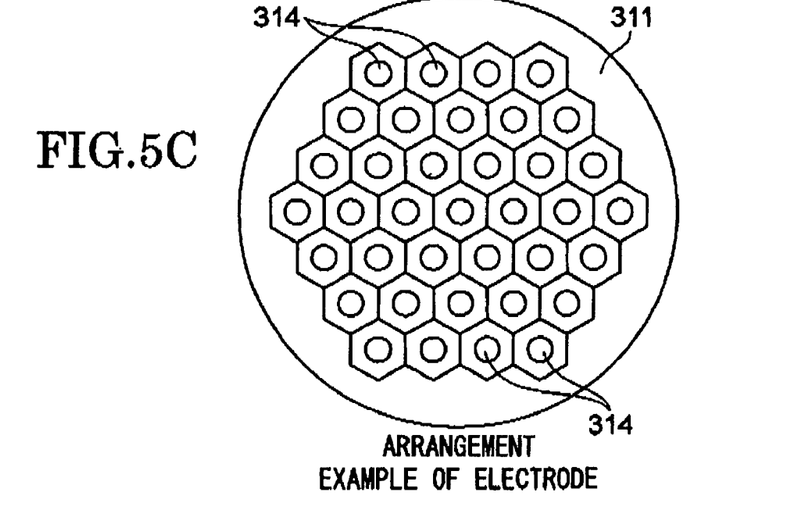
FIG. 5C is a view that illustrates an arrangement example of electrodes of the deformable mirror device.
Figure 6:
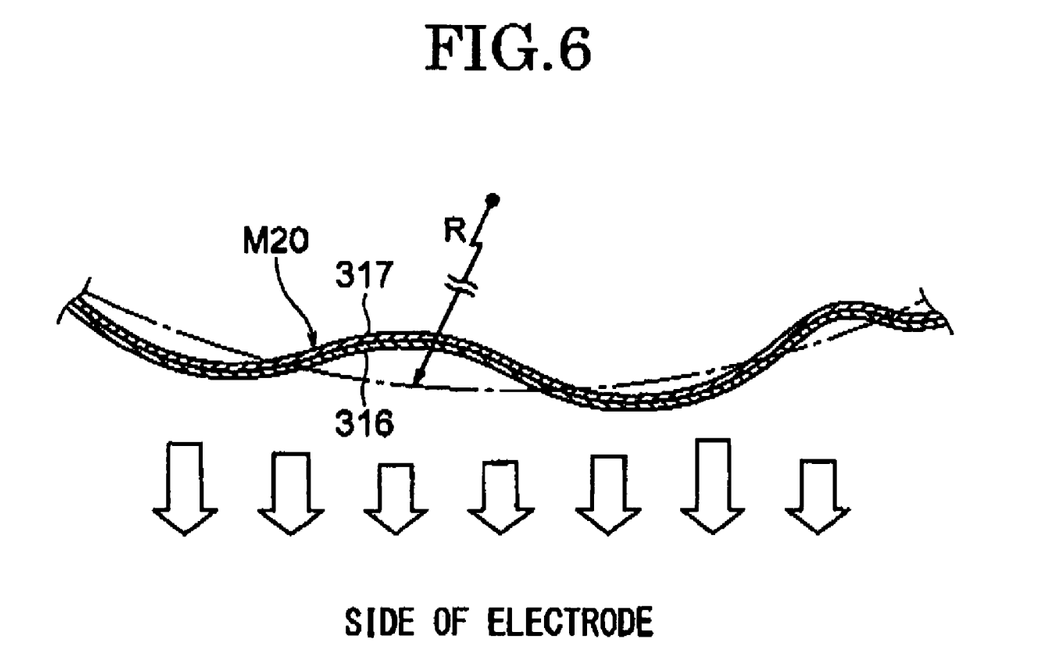
FIG. 6 is an enlarged cross-sectional view of a portion of the deformable minor M20 of the high-magnification retina image photographing control system of embodiment 1.

FIG. 3 is a schematic control system diagram that illustrates the high-magnification retina image photographing control system of the embodiment 1. FIG. 4 is a schematic diagram that illustrates the wavefront sensor 29 of the high magnification retina image photographing control system of the embodiments 1. FIG. 5A illustrates a plan view illustrating an example of the deformable mirror apparatus of the high-magnification retina image photographing control system of the embodiment 1. FIG. 5B illustrates a sectional view by the A-A line in FIG. 5A. FIG. 5C illustrates the arrangement example of the electrodes. FIG. 6 is an enlarged cross-sectional view illustrating a portion of the deformable mirror M20 of the high-magnification retina image photographing control system of the embodiment 1.

The high-magnification retina image photographing control system of the embodiment 1 includes, as shown in FIG. 3, a first focus adjustment motor actuator 26, the VCC adjustment motor actuator 27, the second focus adjustment piezo actuator 28, the wavefront sensor 29, a deformable mirror device 31, and a retina image photographing controller 32. In addition, the illustration of the light source of the wavefront sensor 29 is abbreviated.

The wavefront sensor 29 includes, as shown in FIG. 4, a Hartmann plate 291 in which micro Fresnel lenses (micro lenses) are arranged in a reticular pattern, and a two-dimensional CCD 292 (two dimensional charge-coupled device) parallelly disposed via a predetermined interval from the Hartmann plate 291.

A point light source is projected on the retina of the eye E, wherein the reflection light reflected by the retina is divided into numerous luminous fluxes by the Hartmann plate 291, the point image position of the respective luminous flux is measured by the two-dimensional CCD 292. By comparing the measured point image position with the point image position of a non-aberration eye, the wavefront aberration appears as the amount of displacement ($\Delta x$, $\Delta y$) of the respective point images on the two dimensional CCD 292. The wavefront aberration is measured by the wavefront sensor 29. The measurement results are used as the input information to deform the deformable mirror M20 into the phase shape opposite to the wavefront. The measurement results are also used as the input information to remove the cylinder component C by the VCC adjustment, to remove the spherical surface component S by the high-magnification low-speed focus adjustment, to remove the infinitesimal spherical surface component S' by the high-magnification high-speed focus adjustment.

The deformable mirror apparatus 31 includes, as shown in FIGS. 5A, 5D, 5C, the electrostatic type deformable mirror M20, an electrode substrate 311, a silicon substrate 312, spacers 313, electrodes 314 and a voltage control circuit 315.

The electrostatic type deformable minor M20 includes a two-layer structure of a membrane 316 on the side of the electrodes 314 and a reflective film 317 on the optical path side. The membrane 316 is manufactured by the selective etching process relative to the silicon substrate 312, possesses flexibility, and has a thickness of about 4 μm. For example, the reflective film 317 is formed by depositing a material having a high reflectance ratio on the membrane 316. For example, a metallic membrane having a high reflectance ratio such as aluminum is used. The spacers 313 are used to maintain the gap length between the membrane 316 and the electrodes 314 to a determined value. For example, a ball with high rigidity is used. A large number of the electrodes 314 are disposed on the electrode substrate 311. For example, as illustrated in FIG. 5C, a large number of hexagonal electrodes are arranged in the shape of a honeycomb. The voltage control circuit 315 is a circuit that drives each individual electrode 314 by voltage. In order to deform the membrane 316 in correspondence to each electrode 314, an electrostatic voltage is applied to each electrode 314.

As illustrated in FIG. 6, the deformable mirror M20 deforms the membrane 316 only by the tension force with the numerous electrodes 314 to which a desired voltage is applied in order to obtain distortion deformation which cancels out the distortion of the wavefront. Therefore, by the deformation as shown by the dashed-dotted line of FIG. 6, the deformable mirror M20 has a plane corresponding to the average deformation volume of the concavity and convexity deformation of the membrane 316 that becomes slightly concave, and infinitesimal spherical diopter by the large radius R is newly generated.

The retina image photographing controller 32 performs automatic adjustment by the cylinder component adjustment mechanism 23 and the high-magnification low-speed focusing mechanism 21 when photographing a high-magnification retina image. After performing the VCC adjustment and the high-magnification low-speed focus adjustment, the retina image photographing controller 32 simultaneously conducts the optical aberration compensation of the eye E by the wavefront aberration compensation system 25 and the automatic adjustment by the high-magnification high-speed focus adjustment 24, and photographs the retina image of the eye E if the RMS (wavefront aberration barometer) based on the aberration measurement value from the wavefront sensor 29 by the optical aberration compensation and the high magnification high speed focus adjustment is converged below a specified value. The aberration compensation algorithm flow is described in detail hereinbelow,

[High Magnification Retina Image Photographing Control Process]

Figure 7:
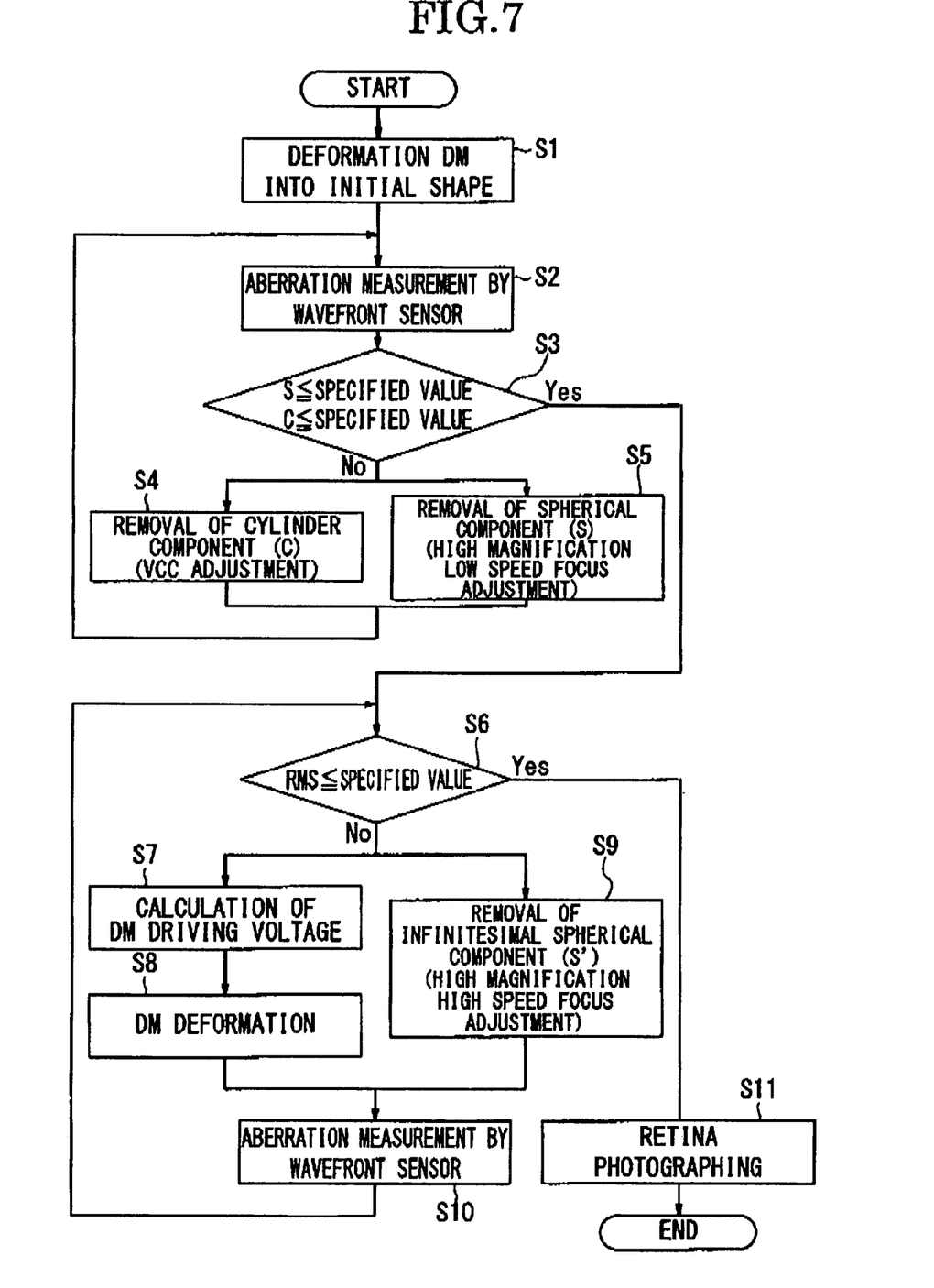
FIG. 7 is a flowchart that illustrates the flow of high-magnification retina image photographing control processing executed by the retina image photographing controller 32 of embodiment 1.

FIG. 7 is a flow chart that illustrates the flow of the high magnification retina image photographing control process to be executed by the retina photographing controller 32 based on the embodiment 1. Each step is described hereinbelow. The process is started by the high magnification retina image photographing operation by the examiner. In addition, the visual axis tracking control process which suppresses the fluctuation of the visual axis direction by involuntary eye movement based on the visual axis detection is simultaneously executed although it is abbreviated in this flow chart.

Step S1 is a step that deforms the deformable mirror M20 into its initial form after the start of the high magnification retina image photographing operation. "The initial form of the deformable mirror M20" has an initial form having the estimated infinitesimal spherical diopter such that the infinitesimal spherical diopter of the deformable mirror M20 is estimated when the aberration compensation is completed. The initial form compensates by mounting an aberration shape onto the infinitesimal spherical shape in the case of the membrane type deformable mirror M20. By securing the preliminarily estimated infinitesimal spherical diopter, the necessary displacement quantity for the high magnification high speed focus system can be suppressed.

Step S2 is a step that performs the aberration measurement by the wavefront sensor 29, followed by the initial form deformation of the deformable mirror M20 in step S1, the VCC adjustment in step S4, or the high magnification low speed focus adjustment in step S5.

In addition, in the embodiment 1, the aberration measurement is performed immediately after the initial form deformation of the deformable mirror M20. Howeyer, for example, after the initial form deformation of the deformable mirror M20, the high magnification low speed focus mechanism 21 is moved to bring the wavefront sensor 29 into a significant domain, and then the aberration measurement of the wavefront sensor 29 can be performed.

Step S3 is a step that determines whether or not a spherical component S is below a specified value and whether or not a cylinder component C is below a specified value, followed by the aberration measurement by the wavefront sensor 29 in step S2. If it is determined Yes in step S3, it moves on to step S6. If it is determined No in step S3, it moves on to stop S4 and step S5.

In this case, the "specified value" of the spherical component S (hyperopia, myopia) and the cylinder component C (astigmatism) is set to the smallest possible value showing high accuracy compensation of the flexing properties of the eyeball such as hyperopia, myopia and astigmatism.

In step S4, following the determination in step S3 of not being S≦a specified value and C≦specified value, the cylinder component C is removed by the cylinder component adjustment mechanism 23 based on the aberration measurement value (astigmatism diopter and astigmatism axis angle) by the wavefront sensor 29, wherein the VCC adjustment motor actuator 27 drives and controls the astigmatism compensation variable cross cylinder lens VCC.

In step S5, following the determination in step S3 of not being S≦a specified value and C≦a specified value, the spherical component S is removed by the high magnification low speed focus mechanism 21 based on the aberration measurement value (spherical diopter) by the wavefront sensor 29, wherein the first focus adjustment motor actuator 26 drives and controls the mirror unit MU.

Step S6 is a step to determine whether or not the RMS value (wavefront aberration barometer) of the total aberration calculated based on the aberration measurement value by the wavefront sensor 29 is below the specified value, followed by the determination in step S3 of S≦a specified value and C≦a specified value or the aberration measurement by the wavefront sensor 29 in step S10. In the step S6, if it is determined Yes, it moves on to step S11, and if it is determined No, it moves on to step S7 and step S9. Here, "RMS" is an abbreviation of root mean square. It denotes the standard deviation (dispersal square root) between the actual wavefront and the ideal wavefront. In addition, the specified value of the RMS value is set to 0.05 μm, for example.

Step S7 is a step that calculates the driving voltage of the deformable mirror M20, followed by the determination of RMS>a specified value in step S6. The calculation of the driving voltage of the deformable mirror M20 uses the distortion generated when applying the voltage to one electrode as an influence function. By superimposing the influence function corresponding to each electrode (the superimposed amplitude is calculated using the least square method), the influence function formula and the like for calculating the voltage arrangement data corresponding to a target shape is used for the calculation of the driving voltage of the deformable mirror M20.

Step S8 is a step to apply on each electrode 314 the driving voltage calculated by the voltage control circuit 315, and to deform the membrane 316 by only the tension power by each electrode 314, followed by the driving voltage calculation of the deformable mirror M20 in step S7.

In step S9, following the determination of RMS>a specified value at step S6, the infinitesimal spherical component S' is removed by the high magnification high speed focusing mechanism 24 based on the aberration measurement value (spherical diopter) by the wave front sensor 29, wherein the second focus adjustment piezo actuator 28 drives and controls the lens L16.

Step S10 is a step that performs the aberration measurement by the wavefront sensor 29, followed by the removal of the infinitesimal spherical component S' in step S9 or the deformation of the deformable mirror M20 in step S8.

Step S11 is a step that performs the retina photographing, followed by the determination of RMS≦a specified value in step S6.

Next, operations are described.

[Anterior Segment Observation and Observation and Photographing Operation of Retina Image with Low Magnification]

First, when performing the anterior segment observation of the eye FE, the examiner lets the examinee sit in a chair (not illustrated) and lets the chin of the examinee be placed on the chin rest 6. And the alignment of the optical system relative to the eye E is performed by moving the trestle 3 with the control leyer 4 in the up-and-down, and left-d-right directions on the base 2, projecting the eye E on the central portion of the color liquid crystal monitor 11, and observing the anterior segment of the eye E.

When performing the retina image observation of the eye E, by straightforwardly pushing the trestle 3 by the control leyer 4 from the anterior segment observation position, the image enters through the pupil, a retina Ef of the eye E is projected out of focus. In this state, for example, by operating a control leyer 4, the two alignment luminescent spots on the color liquid crystal monitor 11 are matched into one spot. Furthermore, by inputting the matched one spot within the "( ) scale" on the color liquid crystal monitor 11, the retina Ef is focused. By projecting the retina Ef of the eye E on the color liquid crystal monitor 11, the retina image of the eye E is observed.

Secondly, when performing the retina image photographing of the eye E, since the retina Ef to be photographed by moving the low magnification focus mechanism 20 is focused, the low magnification photographing of the clear retina image of the eye E can be end by only performing the pressing operation of the photographing button 4a. The photographing data, for example, can be recorded on film or filed as an electronic image.

[Retina Image Photographing Effects by High Magnification]

The examiner, along with choosing the photographing magnification of the high magnification retina photographing system 104 according to an object, moves the fixation target light source OS4, shifts the visual axis direction of the examinee, adjusts a desired photographing position on the position of a mark (for example, a rectangular mark) of the color liquid crystal monitor 11, and identifies the photographing position to be photographed by the high magnification retina photographing system 104.

Thereafter, if the examiner performs the photographing operation of the high magnification retina image, the visual axis tracking control process for controlling the fluctuation in the visual axis direction by the involuntary eye movement based on visual axis detection is performed, and also the photographing process of the high magnification retina image is executed according to the flow chart shown in FIG. 7.

The photographing process of the high magnification retina image, in the flow chart of FIG. 7, is processed in a sequence of step S1→step S2→step S3→step S4 and step S5. Unless the removal condition of the spherical component S in step S3 and the removal condition of the cylinder component C in step S3 are realized, the sequential flow from step S2→step S3→(step S4 and step S5) is repeated.

More specifically, when photographing the high magnification retina image, the deformable mirror M20 is deformed to its initial form (step S1), afterwards, the aberration measurement is performed by the wavefront sensor 29 (step S2), and the compensation of the spherical component S by the optical path length adjustment by the mirror unit MU (step S5) and the compensation of the cylinder component C by the adjustment of the astigmatism compensation variable cross cylinder lens VCC (step S4) are simultaneously performed under a low-speed compensation process.

By executing the low-speed compensation process, when the spherical component S and the cylinder component C fall below the specified value based on an aberration measurement value, in the flow chart of FIG. 7, it is processed sequentially from step S3 to step S6, the low-speed compensation process is stopped and the high-speed compensation process of step S6 to step S10 is started.

When the high-peed compensation process is started, unless the wavefront aberration removal condition is realized (step S6), the sequential flow of step S6→(step S7→step S8 and step S9)→step S10 is repeated.

That is to say, the driving voltage of the deformable mirror M20 is calculated (step S7), and the control to deform the deformable mirror M20 (step S8) and the removal of the infinitesimal spherical component S' by the high magnification high speed focus mechanism 24 (step S9) are simultaneously performed under the high speed compensation process.

By implementing the high speed compensation process, when the RMS value based on an aberration measurement value converges below the specified value, in the flow chart of FIG. 7, it is sequentially processed from step S6 to step S11. The high speed compensation process is stopped and the retina image of the eye E is photographed at high magnification. The photographing data is, for example, recorded on film or filed as an electronic image. In this case, the aberration data when photographing is also preferably recorded. In addition, the fixation target data and the low magnification image data can be recorded so that a high magnification photographing position can possibly be identified.

As described above, in the ophthalmologic apparatus 1 of embodiment 1, by having the cylinder component adjustment mechanism 23 and the high magnification low speed focusing mechanism 21 within the optical path of the photographing system, the focusing of the retina image of the eye E is performed according to the refractive properties of the eye E (for example, myopia, hyperopia and astigmatism). After the adjustment by the high magnification low speed focus mechanism 21 and the cylinder component adjustment mechanism 23, by the high magnification high speed focus mechanism 24 within the optical path of the photographing system, the infinitesimal spherical aberration generated by the aberration compensation system 25 is compensated.

In addition, against an infinitesimal spherical aberration newly generated by the aberration compensation system 25, further compensation adjustment by the high magnification low speed focus mechanism 21 can be achieyed.

Howeyer, in this instance, it is composed in the sequential of the focusing by the high magnification low speed focus mechanism 21 and the cylinder component adjustment mechanism 23→the compensation of the optical aberration of the eye E by the aberration compensation system 25→the focusing by the high magnification low speed focus mechanism 21. The degree of accuracy and the degree of responsiveness is low in terms of the compensation adjustment by the infinitesimal spherical aberration by the high magnification low speed focus mechanism 21.

Because the high magnification low speed focusing mechanism 21 is an approximate focusing device that adjusts the optical path length. In comparison to requiring slight optical path length adjustment relative to the newly generated infinitesimal spherical aberration, the optical path length variation quantity (control quantity) of a single control order is large so that in the case of performing slight adjustment of the optical path length, it is necessary to gradually reciprocate by multiple times control orders thus bringing closer to the objective displacement quantity. Because the control quantity is large, precision to conform to the objective displacement quantity can not be attained. In addition, because it is a reciprocated control of multiple times, a long running-in time is required.

Therefore, as a matter of practice, the high magnification low speed focus mechanism 21 cannot perform appropriate aberration compensation in correspondence to the infinitesimal spherical diopter newly generated by the deformable mirror M20, and aberration by the infinitesimal spherical diopter remains. Alternatively, even when performing the compensation of the infinitesimal spherical diopter, the time required for the compensation is too long.

At the same time, in embodiment 1, the high magnification low weed focus mechanism 21 and the cylinder component adjustment mechanism 23 share the focusing function that compensates the refractive properties of the eye E. The high magnification high speed focus mechanism 24 supplemented in the optical path of the photographing system shares the focusing function that compensates the newly generated infinitesimal spherical aberration.

By adopting the composition that shares the focusing function, without being influenced by the high magnification low speed focus mechanism 21 and the cylinder component adjustment mechanism 23, the degree of accuracy and responsiveness is ensured by the focusing properties possessed by the high magnification high speed focus mechanism 24, and the newly generated infinitesimal spherical aberration accompanying the aberration compensation is appropriately compensated.

For example, like in embodiment 1, by using the second focus adjustment piezo actuator 28 as the high magnification high speed focus mechanism 24, the infinitesimal quantity movement along the optical axis direction can be controlled so that the precision or responsiveness can be ensured.

With regard to the responsiveness, by selecting a highly responsive actuator, the responsiveness not only improves, but like the retina image photographing controller 32 in embodiment 1, the responsiveness can be further improved by adopting the following method.

The adoption of the high speed compensation process that simultaneously performs the compensation of the infinitesimal spherical component S' by adjusting the lens L16 that constitutes the imaging system and the deformational control of the deformable mirror M20

In this case, after the deformational control of the deformable mirror M20 ends, processing time is shortened in comparison to the situation wherein the compensation of an infinitesimal spherical component S' is made by a high magnification high speed focus mechanism 24.

The adoption of a method that preliminarily deforms the deformable mirror M20 into initial forms by the infinitesimal spherical surface when it begins photographing of a high magnification retina image.

In this situation, in comparison to the case where the deformable minor M20 is not initially deformed, the necessary stokes for the second focus adjustment piezo actuator 28 can be reduced so that the actuator can be downsized, and the further speeding up of the actuator can be achieved.

As described above, since the high magnification high speed focus mechanism 24 compensates the newly generated infinitesimal spherical aberration accompanying the aberration compensation with high precision and high speed, in comparison to the case where the infinitesimal spherical aberration remains, the resolution of the retina image is further increased, and an extremely clear retina image can be obtained eyen with high magnification.

Next, effects are explained

The ophthalmologic photographing apparatus 1 according to embodiment 1 can provide the effects listed below.

(1) The ophthalmologic apparatus according to embodiment 1 includes the imaging system that illuminates the retina Ef of the eye E, and images the retina of the eye E based on reflective luminous flux from the retina Ef, the aberration measurement part that measures the optical aberration of the eye E, the aberration compensation device disposed in the imaging system to compensate the optical aberration of the eye E based on a signal from the aberration measurement part, the first focusing device disposed in the optical path of the imaging system to perform focusing of the image of the retina Ef of the eye E according to the refractive property of the eye E, and the second focusing device disposed in the optical path of the imaging system to compensate the infinitesimal spherical aberration generated by the aberration compensation device after the adjustment by the first focusing device. Therefore, an extremely clear image of the retina eyen with a high magnification can be obtained with high accuracy and high speed by compensating the infinitesimal spherical aberration newly generated accompanying with the aberration compensation.

(2) The first focusing device is a device that compensates the spherical diopter component and the astigmatism diopter component of the wavefront aberration generated because of the flexing property of the eye E, the aberration compensation device is a device that compensates the remaining portion which is not corrected by the compensation of the spherical diopter component and the astigmatism diopter component and the higher-order wavefront aberration component by deforming the deformable mirror M20, and the second focusing device is a device that compensates the wavefront aberration component by the infinitesimal spherical diopter newly generated by deforming the deformable mirror M20. Accordingly, all of the wavefront aberration components constituted by the infinitesimal spherical diopter, the higher-order wavefront aberration component, the astigmatism diopter component, and the spherical diopter component, which are the causes of hindering the clarity of the retina image when turned into high magnification, can be removed.

(3) The device that compensates the spherical diopter component of the first focusing device is the high magnification low speed focus mechanism 21 that adjusts the length of the optical path by moving the two total reflective mirrors M11, M12 orthogonal to each other disposed in the optical path of the imaging system along the optical axis direction by the first focus adjustment motor actuator 26. Accordingly, the spherical diopter component (myopia or hyperopia) of the wavefront aberration generated because of the refractive properties of the eye E can be compensated by adjusting the optical path length to be determined by the position of the mirror unit MU.

(4) The device to compensate the astigmatism diopter component of the first focusing device is the cylinder component adjustment mechanism 23 that adjusts the cylinder diopter and the axis angle by reyersing the optical axis the astigmatism compensation variable cross cylinder lens VCC disposed in the optical path of the imaging system by the VCC adjustment motor actuator 27. Accordingly, within the wavefront aberration generated because of the refractive properties of an eye E, of the astigmatism diopter component (astigmatism), within the combination of the two cylinder lenses that constitutes the astigmatism compensation variable cross cylinder lens VCC, the astigmatism diopter can be compensated by reyersing the optical axis of one of the cylinder lenses, and the astigmatism axis can be compensated by reyersing the optical axis on the whole.

(5) The second focusing device is the high magnification high speed focus mechanism 24 that controls the infinitesimal quantity movement of at least a portion of a lens of the lens system that constitutes the imaging system along the optical axis direction by the second focus adjustment piezo actuator 28. Therefore, by high precision and high responsiveness, the wavefront aberration portion by the newly generated infinitesimal spherical diopter can be compensated by deforming the deformable minor M20 while maintaining the compact system such that a new lens or the like is not required to be added into the imaging system.

(6) The aberration measurement part includes the Hartmann plate 291 in which the micro lenses are arranged in a lattice shape and the two-dimensional charge coupled device 292, and the aberration measurement part is the wavefront sensor 29 that projects a point light source on the retina of the eye E, divides by the Hartmann plate 291 the reflective light reflected by the retina into numerous luminous flux, measures by the two-dimensional charge coupled device 292 the image point position by the respective luminous flux, and compares the point image position with the instance of a no aberration eye, so as to measure the wavefront aberration of the eye E. Wavefront aberration as the input information that determines whether a clear image of the retina can be obtained is measured with high precision. That is to say, when photographing the retina image with high magnification, the measurement results by the wavefront sensor 29 are used as the input information to deform the deformable mirror M20 into a phase shape opposite to the wavefront, and also are used as the input information to remove the infinitesimal spherical component S' by the high magnification high speed focus adjustment and to remove the spherical component S by the high magnification low speed focus adjustment and to remove the cylinder component C by the VCC adjustment.

(7) Since the retina photographing controller 32 that performs the automatic adjustment by the first focusing device when photographing the image of the retina with a high magnification, after the first focusing adjustment, simultaneously performs the optical aberration compensation of the eye by the aberration compensation device and the automatic adjustment by the second focusing device, and photographs the image of the retina of the eye when the wavefront aberration converges by the second focusing adjustment is provided, a clear ocular funds image with a high magnification can be automatically obtained with a good response from the start of the operation by conducting the photographing start operation without requiring a manual focus adjustment operation.

(8) The retina image photographing controller 32 deforms in advance the deformable mirror M20 into the initial form by the infinitesimal spherical surface when photographing the image of the retina with a high magnification, starts the low speed compensation process that simultaneously performs the compensation of the spherical diopter component S by the adjustment of the length of the optical path by the mirror unit MU and the compensation of the cylinder component C by the adjustment of the astigmatism compensation variable cross cylinder lens VCC, when the spherical diopter component S and the cylinder component C based on the aberration measurement value falls below a specified value by the implementation of the low speed compensation process, in continuation of stoppage of the low speed compensation process, starts the high speed compensation process that simultaneously performs the deformational control of the deformable mirror M20 and the infinitesimal spherical diopter component S' compensation by the adjustment of the lens L16 that constitutes the photographing system, and when the RES value based on the aberration measurement value converges below a specified value by the implementation of the high speed compensation process, all of the spherical component S, the cylinder component C, the higher-order wavefront aberration component and the infinitesimal spherical component S' are eliminated by the automatic adjustment operation with high response by conducting the photographing start operation for photographing the ocular funds image of the eye E, and photographs an extremely high ocular funds image with a high magnification. Namely, when allowable resolution of the ocular funds image is determined, high magnification degree can be further improved according to the requirement of high magnification.

Although the present invention has been described in terms of the embodiment 1, it is not limited thereto. It should be appreciated that variations may be made in embodiment 1 by a person skilled in the art without departing from the scope of the present invention as defined by the following claims.

In embodiment 1, an example was described whereby when photographing the high magnification retina image, the automatic adjustment by the first focusing device is implemented, and after the first focus adjustment is completed, the optical aberration compensation of the eye by the aberration compensation device and the automatic adjustment by the second focusing device are simultaneously conducted, and the retina photographing controller 32 that photographs the retina image of the eye E when the wavefront aberration converges by the second focusing adjustment is provided. Howeyer, with the exception of the optical aberration compensation of the eye by the aberration compensation device, the focusing adjustment can be manually operated instead of being automatically controlled. In short, the present invention is not limited to embodiment 1, as long as the ophthalmologic apparatus includes in the optical path of the imaging system the first focusing device that performs the focusing of the retina image of the eye according to the refractive properties of the eye and the second focusing measure that compensates the infinitesimal spherical aberration generated by the aberration compensation device after the adjustment by the first focusing device.

Therefore, in the ophthalmologic apparatus according to the present invention, the first focusing device disposed in the optical path of the photographing system performs the focusing of the retina image of the eye according to the refractive property of the eye. Then, after the adjustment by the first focusing device, the second focusing device disposed in the optical path of the photographing system compensates the infinitesimal wavefront aberration generated by the aberration compensation device.

That is to say, the first focusing device is assigned the focusing function that compensates the refractive property of the eye. The second focusing device disposed in the optical path of the imaging system is assigned the focusing function that compensates the newly generated infinitesimal spherical aberration. By adopting the configuration of assigning separately the focusing function, without having the influence of the first focusing device, the newly generated infinitesimal spherical aberration accompanying the aberration compensation is compensated properly while securing the accuracy and responsiveness by the focusing properties of the second focusing device. The resolution of the retina image thereby is further improved in comparison to an instance where infinitesimal spherical aberration remains.

In such a way, an extremely clear retina image can be obtained eyen with high magnification by compensating the newly generated infinitesimal spherical aberration accompanying with the aberration compensation with high accuracy and high speed.

While a preferred embodiment of the invention has been described and illustrated above, it should be understood that this is exemplary of the invention and is not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An ophthalmologic apparatus, comprising:
   an imaging system that illuminates a retina of an eye, and images the retina of the eye based on reflective luminous flux from the retina;
   an aberration measurement part that measures optical aberration of the eye;
   an aberration compensation device disposed in the imaging system to compensate the optical aberration of the eye based on a signal from the aberration measurement part;
   a first focusing device disposed in an optical path of the imaging system to perform focusing of an image of the retina of the eye according to a refractive property of the eye; and
   a second focusing device disposed in the optical path of the imaging system to compensate an infinitesimal spherical aberration generated by the aberration compensation device after adjustment by the first focusing device, and wherein
   the first focusing device is a device that compensates a spherical diopter component and an astigmatism diopter component of a wavefront aberration generated because of a flexing property of the eye and,
   the second focusing device is a high-magnification high-speed focus mechanism that compensates a wavefront aberration component, that is, an infinitesimal spherical diopter newly generated by deforming the deformable mirror and controls infinitesimal quantity movement of at least a portion of a lens of a lens system that constitutes the imaging system along an optical axis direction by a piezo device.

2. An ophthalmologic apparatus as set forth in claim 1, wherein the device that compensates the spherical diopter component of the first focusing device is a high-magnification low-speed focus mechanism that adjusts a length of the optical path by moving a reflective member having two orthogonal reflective parts disposed in the optical path of the imaging system along an optical axis direction by a first motor device.

3. An ophthalmologic apparatus as set forth in claim 1, wherein the device to compensate the astigmatism diopter component of the first focusing device is a cylinder component adjustment mechanism that adjusts a cylinder diopter and an axis angle by turning around an optical axis an astigmatism compensation cylinder lens disposed in the optical path of the imaging system by a second motor device.

4. An ophthalmologic apparatus comprising:
   an imaging system that illuminates a retina of an eye, and images the retina of the eye based on reflective luminous flux from the retina;
   an aberration measurement part that measures optical aberration of the eye;
   an aberration compensation device disposed in the imaging system to compensate the optical aberration of the eye based on a signal from the aberration measurement part;
   a first focusing device disposed in an optical path of the imaging system to perform focusing of an image of the retina of the eye according to a refractive property of the eye;
   a second focusing device disposed in the optical path of the imaging system to compensate an infinitesimal spherical aberration generated by the aberration compensation device after adjustment by the first focusing device; and
   a retina photographing control device that performs automatic adjustment by the first focusing device when photographing the image of the retina with a high magnification, after the first focusing adjustment, simultaneously performs the optical aberration compensation of the eye by the aberration compensation device and the automatic adjustment by the second focusing device, and photographs the image of the retina of the eye when the wavefront aberration converges by the second focusing adjustment, wherein
   the retina image photographing control device deforms in advance a deformable mirror into an initial form by an infinitesimal spherical surface when photographing the image of the retina with a high magnification, starts a low-speed compensation process that simultaneously performs spherical diopter component compensation by adjustment of a length of the optical path by a reflective member and an astigmatism diopter component compensation by adjustment of an astigmatism compensation cylinder lens, when the spherical diopter component and the astigmatism diopter component based on an aberration measurement value falls below a specified value by the implementation of the low speed compensation process, in continuation of stoppage of the low speed compensation process, starts a high-speed compensation process that simultaneously performs deformational control of the deformable mirror and infinitesimal spherical diopter component compensation by adjustment of a lens that constitutes the photographing system, and when a barometer of wavefront aberration based on an aberration measurement value converges below a specified value by the implementation of the high-speed compensation process, photographs the image of the retina of the eye.

5. An ophthalmologic apparatus as set forth in claim 4, wherein:
   the second focusing device is a high-magnification high-speed focus mechanism that compensates a wavefront aberration component, that is, an infinitesimal spherical diopter newly generated by deforming the deformable mirror and controls infinitesimal quantity movement of at least a portion of a lens of a lens system that constitutes the imaging system along an optical axis direction by a piezo device.

6. An ophthalmologic apparatus as set forth in claim 4, wherein:
   the device that compensates the spherical diopter component of the first focusing device is a high-magnification low-speed focus mechanism that adjusts a length of the optical path by moving a reflective member having two orthogonal reflective parts disposed in the optical path of the imaging system along an optical axis direction by a first motor device, and
   the device that compensates the astigmatism diopter component of the first focusing device is a cylinder component adjustment mechanism that adjusts a cylinder diopter and an axis angle by turning around an optical axis an astigmatism compensation cylinder lens disposed in the optical path of the imaging system by a second motor device.

* * * * *